United States Patent
Kang et al.

(10) Patent No.: US 6,518,484 B2
(45) Date of Patent: Feb. 11, 2003

(54) PROMOTER SYSTEM OF PLANT TRANSLATIONALLY CONTROLLED TUMOR PROTEIN GENE

(75) Inventors: Jeong-Gu Kang, Kwangju (KR); Ju Yun, Kwangju (KR); Kyung-Sook Chung, Kwangju (KR); Pill-Soon Song, Kwangju (KR); Chung-Mo Park, Kwangju (KR)

(73) Assignee: Korea Kumho Petrochemical Co., Ltd. (KR)

( * ) Notice: Subject to any disclaimer, the term of this patent is extended or adjusted under 35 U.S.C. 154(b) by 0 days.

(21) Appl. No.: 09/815,622

(22) Filed: Mar. 23, 2001

(65) Prior Publication Data

US 2002/0108141 A1 Aug. 8, 2002

(30) Foreign Application Priority Data

Dec. 28, 2000 (KR) ............................................ 00-84642

(51) Int. Cl.$^7$ ............................. A01H 1/00; A01H 5/00; C07H 21/02; C07H 21/04; C12N 5/04; C12N 15/82
(52) U.S. Cl. ...................... 800/287; 800/298; 536/23.1; 536/24.1; 435/419; 435/468
(58) Field of Search ................................ 800/287, 298; 536/24.1, 23.1; 435/415, 468

(56) References Cited

PUBLICATIONS

GenBank Assession No. AT3G16640, 2001.*
Nemeth et.al.; Pleiotropic control of glucose and hormone responses by PRL1, a nuclear WD protein, in Arabidopsis, 1998, Genes & Development 12:3059–3073.*
Puente et.al.; Comjbinatorial interplay of promoter elements constitutes the minimal determinants for light and development control of gene expression in Arabidopsis; 1996, The EMBO Journal, vol. 15: 3732–3743.*
Kim, K. et al., Plant Physiology, 1999, vol. 121, pp. 225–236, Identification of cis–Acting Elements Important for Expression of the Starch–Branching Enzyme I Gene in Maize Endosperm[1].
Park, S. et al., Plant Physiology 1996, vol. 112, pp. 1563–1571, Cis–Acting Elements Essential for Light Regulation of the Nuclear Gene Encoding the A Subunit of Chloroplast Glyceraldehyde 3– Phosphate Dehydrogenase in *Arabidopsis thaliana*.
MacDonald, S. et al., Science vol. 269, 1995, pp. 688–690, Molecular Identification of an IgE–Dependent Histamine–Releasing Factor.
Clough, S. et al., The Plant Journal 1998, vol. 16(6), pp. 735–743, Floral Dip: A simplified method for Agrobacterium–mediated transformation of *Arabidopsis thaliana*.
Yannick, G. et al., Biochemical Society Transactions 1997, vol. 25, p. 269S Intracellular colocalisation of the translationally controlled protein P23 with cytoskeletal structures.
Yannick, G., et al., Journal of Cell Science, vol. 112, pp. 1257–1271, 1999. The growth–related, translationally controlled protein P23 has properties of a tubulin binding protein & associates transiently w/ microtubules during the cell cycle.
Xu, P. et al., Biochemical Society, 1999, vol. 342, pp. 683–689, Expression of translationally controlled tumor protein is regulated by calcium at both the transcriptional and post–transcriptional level.
Sanchez, J. et al., Electrophoresis, 1997, pp. 150–155, Translationally controlled tumor protein: A protein identified in several nontumoral cells including erthrocytes.
Wu, Y. et al., Science vol. 278, 1997, pp. 2126–2130, Abscisic Acid Signaling Through Cyclic ADP—Ribose in Plants.
Woo,H. et al., Plant Molecular Biology, vol. 35: pp. 1045–1051, 1997, Cloning of genes whose expression is correlated with mitosis and localized in dividing cells in root caps of *Pisum sativaum* L.
Sage–Ono, K. et al., Plant Cell Physiology, 1998, vol. 39(3), pp. 357–360, Dark–Induced Accumulation of mRNA for a Homolog of Translatinally Controlled Protein (TCTP) in Pharbitis.
Yoshida, K. et al., Proc. Nat'l. Acad. Sci. vol. 90, pp. 6636–6640, 1993, Phytochrome–regulated expression of the genes encoding the small GTP–binding proteins in peas.
Nagano, Y. et al., Proc. Nat'l. Acad. Sci. vol. 92, pp. 6314–6318, 1995, Location of light–repressible, small GTO YPT/rab family in the growing zone.
Shusei Sato et al., Structural Analysis of *Areabidopsis thaliana* Chomosome 3. I Sequence Features of the Regions of 4,504,864 bp Covered by Sixty P1 and TAC Clones, DNA Res., 2000, 7:131–135.

* cited by examiner

*Primary Examiner*—Elizabeth F. McElwain
*Assistant Examiner*—Stuart Baum
(74) *Attorney, Agent, or Firm*—Mathews, Collins, Shepherd & McKay, P.A.

(57) ABSTRACT

The present invention provides a nucleic acid molecule isolated from the 5' untranscribed region of a translationally controlled tumor protein (TCTP) gene from Arabidopsis. The nucleic acid molecule, referred to as TCTP promoter in the present invention, directs the high-level expression of a reporter gene that is properly placed under its control. The TCTP promoter initiates and regulates the gene expression to a level that is comparable to those by the currently available promoters in plant genetic engineering. A minimum of 300-bp region is enough for fill regulatory activity. The TCTP promoter is functional in all plant tissues tested with the highest activity in the meristem tissue of root tip. The present invention can be utilized to express useful genes to a high level in agronomically important plants.

7 Claims, 6 Drawing Sheets

FIG. 1

```
-2037  TCCATAAGATGCAGAAATATTACAGTAACACAGATCTTACCCTGTAATTCTTCCATGGTG
-1977  CATGCCACTCTGGACGGGGCCATCTACTAGGCATTCTCTCCATTAAAGCAGCAGTTGACA
            Primer 1
-1917  GATTTCTGTAACACATAGAGGGGAAATGATGGACAAATAATGAATAACTGAAGCATTGAT
-1857  ACAAGTTAGATGCATTTCAGGTTAAATAAATATGGCCAAATTTAAATTTCATGACTCTGA
-1797  ACCACCAATTCACCTTAGTGCGGCTTTATGTACCACCTAGGTATCGCAATCTAGATGTAG
-1737  TGTCGTTATAGAGAGTCCATAAAAGTAGATAAGGATGCGACACAAACCTTTCGGAAAATG
-1677  ATCCAGGTGCAGGAAGAATGGCCGTGCTTTTGCCTGGATTACCAGTATTGTTCCTTCAAT
-1617  TCAAGAATCAATAATTATCAGTATCAATCAGCACGATAAGTAGAGCATCAATCACAAAGA
-1557  CAAAACAGGAATAACATTCTTGAGAATGTCGTAAATTATTTATACTAACTATATGGACTA
-1497  GTCACATTCCAAATGAAATGTATACTCACAAGTCTCTTGGCGGTAAAGTTGGACCAACA
-1437  ACTAAAGCTTTCTCTGTTGCGCTTTTTCGAAGTTCCTTGGAC***CCTTTTG***GACCTGCGGAG
                                             GA-responsive
-1377  AAAATAATTTGGTCTTTCAGAACG***AGAAACAA***TAGTCATGAAAAAGGCTAAAAGATTACA
                                Light-responsive-1
-1317  CTAACAGCGTTTTTAGTGCAGCAGAAGTTTGTTTGAAAAGATACTCTTAAGAGGATACAT
                              Primer 2
-1257  TACTGAAACTTGTTTTCCAATCCTAATTATAGACATATATGAATGAAACTCACAACTAAT
-1197  ATAAATAGATATCAGGGAAACTAGAAAATAGGAAACTAGTTTTGTCTCACAACAGGAAAA
-1137  ACAGATAAAAGAACTACCTGGAAGCGCAAGGGCTTTCAATGGAGCCGTCTTTTCACTGTT
-1077  ATGGTCAGCAATACGTGTAGGCTTACTTGCAGGTTCTACGCCTCCAAATGCAACTTGAAT
-1017  CTATACAAGTAACGTCCAAGTCATTAACTTTTATATTCTACTTGATGTTCACTAAAACGC
 -957  TTGATGCAAACTAAACATCTTACTATAAAGATGAGGGTAATATGCTAGAAAGCAAACTCA
 -897  AACAATAGTAGCTGATGAGAAGAATCTAACTCCAGATAAAAGGTAAACTATAAAAGTGAT
 -837  AAGCCATTGACTGTTCGATTTACACCTTATAAAATTTTCTCAGGTTCAACGTCTCTGAAG
 -777  CTTGCTATAA***AGCTATCCA***TTATCAAACTCAAAACAAAGAAGAAGCGAACAAAATTTTCA
                  Light-responsive-2
 -717  ACACGATCAAAGATAAAATTTAAAAAATATTCGAAAACCCCCTTACCTTATGGCAGAGCC
                                                           Primer 3
 -657  GAATTCTTTTGCTGCGAGACAAGAACAAAAACAGACAAGAAGAAGAAATCGTCAATACAC
 -597  ATAAAAATTCTGAGAAATTTCGAGAAAAAAAAGTGGACATTGCAAGCGAAACTGTTGATT
 -537  AACCTTTCAGGATCAGGCTGAGGAAATTGGCCATGGACGGGGGAGAAAATTTCACGAGCT
 -477  CGTCTAACAGATTTTAGACTGAGTTTTTTCAGTGACTGAGTTTCGACCTCCCTGTTCAAA
 -417  GCTATCATCGTCATTCTAGGGTTTTACACGAACAATCAGAAACAGAACGAGAAAGACGGA
                                     CAAT box?
 -357  AGAGAAGAGAGGGAAATAGGATTTTATCCGACCCGAACACTATTTATACGTAGCCCAACA
 -297  CTCGAATCCCCACCCGTTGGACCAAACCCGGCTCATTAAGCGTCGGTTCAGATTTATTTC
             Primer 4
 -237  CTTTATTTAAAAAAAGGAAAGGGTAAAAAATAGAAAATTGGAAACAGTTAAAGCCCAAA
 -177  ATTGTAATTTACCGAGAATTGTAAATTTACCTGAAAACCCTACGCTATAGTTTCGACTAT
 -117  AAATACCAAACTTAGGACCTCACTTCAGAATCCCCTCGTCGCTGCGTCTCTCTCCCGCAA
  -57  CCTTCGATTTTCGTTTATTCGCATCCATCGGAGAGAGAAAACAATCAATAAGCGACCATG
              Primer 5
```

FIG. 2

A. Promoter Region of *Arabidopsis TCTP* Gene

B. TCTP Promoters

C. CaMV 35S Promoter

SEQUENCE LISTING

<160> NUMBER OF SEQ ID NOS: 3

<210> SEQ ID NO 1
<211> LENGTH: 2181
<212> TYPE: DNA
<213> ORGANISM: Arabidopsis thaliana

<400> SEQUENCE: 1

| | | | | | |
|---|---|---|---|---|---|
| tgacccaacc | caagtgtccc | tggagcacct | gtcaaccaaa | aaatgcatca | attcataaga | 60 |
| acataaagta | ctctctggac | gccaacaaat | ggcctaagaa | tacctacaca | cttaaatgtt | 120 |
| atatccataa | gatgcagaaa | tattacagta | acacagatct | taccctgtaa | ttcttccatg | 180 |
| gtgcatgcca | ctctggacgg | ggccatctac | taggcattct | ctccattaaa | gcagcagttg | 240 |
| acagatttct | gtaacacata | gaggggaaat | gatggacaaa | taatgaataa | ctgaagcatt | 300 |
| gatacaagtt | agatgcattt | caggttaaat | aaatatggcc | aaatttaaat | ttcatgactc | 360 |
| tgaaccacca | attcacctta | gtgcggcttt | atgtaccacc | taggtatcgc | aatctagatg | 420 |
| tagtgtcgtt | atagagagtc | cataaaagta | gataaggatg | cgacacaaac | ctttcggaaa | 480 |
| atgatccagg | tgcaggaaga | atggccgtgc | ttttgcctgg | attaccagta | ttgttccttc | 540 |
| aattcaagaa | tcaataatta | tcagtatcaa | tcagcacgat | aagtagagca | tcaatcacaa | 600 |
| agacaaaaca | ggaataacat | tcttgagaat | gtcgtaaatt | atttatacta | actatatgga | 660 |
| ctagtcacat | tccaaatgaa | aatgtatact | cacaagtctc | ttggcggtaa | agttggacca | 720 |
| acaactaaag | ctttctctgt | tgcgcttttt | cgaagttcct | tggacccttt | tggacctgcg | 780 |
| gagaaaataa | tttggtcttt | cagaacgaga | acaatagtca | tgaaaaagg | ctaaaagatt | 840 |
| acactaacag | cgtttttagt | gcagcagaag | tttgtttgaa | agatactct | taagaggata | 900 |
| cattactgaa | acttgttttc | caatcctaat | tatagacata | tatgaatgaa | actcacaact | 960 |
| aatataaata | gatatcaggg | aaactagaaa | ataggaaact | agttttgtct | cacaacagga | 1020 |
| aaaacagata | aagaactac | ctggaagcgc | aagggctttc | aatggagccg | tcttttcact | 1080 |
| gttatggtca | gcaatacgtg | taggcttact | tgcaggttct | acgcctccaa | atgcaacttg | 1140 |
| aatctataca | agtaacgtcc | aagtcattaa | cttttatatt | ctacttgatg | ttcactaaaa | 1200 |
| cgcttgatgc | aaactaaaca | tcttactata | aagatgaggg | taatatgcta | gaaagcaaac | 1260 |
| tcaaacaata | gtagctgatg | agaagaatct | aactccagat | aaaaggtaaa | ctataaaagt | 1320 |
| gataagccat | tgactgttcg | atttacacct | tataaaattt | tctcaggttc | aacgtctctg | 1380 |
| aagcttgcta | taaagctatc | cattatcaaa | ctcaaaacaa | agaagaagcg | aacaaaattt | 1440 |
| tcaacacgat | caaagataaa | atttaaaaaa | tattcgaaaa | ccccttacc | ttatggcaga | 1500 |
| gccgaattct | tttgctgcga | gacaagaaca | aaaacagaca | agaagaagaa | atcgtcaata | 1560 |
| cacataaaaa | ttctgagaaa | tttcgagaaa | aaaagtgga | cattgcaagc | gaaactgttg | 1620 |
| attaacctttt | caggatcagg | ctgaggaaat | tggccatgga | cggggagaa | aatttcacga | 1680 |
| gctcgtctaa | cagattttag | actgagttt | ttcagtgact | gagtttcgac | ctccctgttc | 1740 |
| aaagctatca | tcgtcattct | agggttttac | acgaacaatc | agaaacagaa | cgagaaagac | 1800 |
| ggaagagaag | agagggaaat | aggattttat | ccgacccgaa | cactatttat | acgtagccca | 1860 |
| acactcgaat | ccccacccgt | tggaccaaac | ccggctcatt | aagcgtcggt | tcagatttat | 1920 |
| ttcctttatt | taaaaaaag | gaaagggtaa | aaaatagaaa | attggaaaca | gttaaagccc | 1980 |
| aaaattgtaa | tttaccgaga | attgtaaatt | tacctgaaaa | ccctacgcta | tagtttcgac | 2040 |

```
tataaatacc aaacttagga cctcacttca gaatcccctc gtcgctgcgt ctctctcccg    2100
caaccttcga ttttcgttta ttcgcatcca tcggagagag aaaacaatca ataagcgacc    2160
atgttggtgt accaagatct t                                              2181
```

<210> SEQ ID NO 2
<211> LENGTH: 29
<212> TYPE: DNA
<213> ORGANISM: Artificial Sequence
<220> FEATURE:
<223> OTHER INFORMATION: synthetic primer for PCR based upon genomic
      clone MGL6 (GenBank Accession No.:AB022217

<400> SEQUENCE: 2

```
gccggatcct gacccaaccc aagtgtccc                                        29
```

<210> SEQ ID NO 3
<211> LENGTH: 31
<212> TYPE: DNA
<213> ORGANISM: Artificial Sequence
<220> FEATURE:
<223> OTHER INFORMATION: synthetic primer for PCR based upon genomic
      clone MGL6 (GenBank Accession No.:AB022217

<400> SEQUENCE: 3

```
gccggatcca agatcttggt acaccaacat g                                     31
```

PROMOTER SYSTEM OF PLANT TRANSLATIONALLY CONTROLLED TUMOR PROTEIN GENE

BACKGROUND OF THE INVENTION

1. Field of the Invention

The present invention relates to a multi-purpose promoter that can be employed to direct the expression of desired genes in genetically engineered plant cells or plants. The invention also provides the expression cassettes and plasmids comprising the 5' untranscribed region of a TCTP gene from Arabidopsis. The reporter gene placed under the control of said promoter in the expression cassettes is ubiquitously expressed to an extremely high level in transgenic plants. In addition, the activity of said promoter is further induced by drought stress. The present invention also provides methods and processes for the preparation of the expression cassettes and transgenic plants comprising the expression cassettes.

2. Description of the Prior Art

In eukaryotic systems gene expression is regulated through complex interactions between various cis-acting and trans-acting regulatory elements. The cis-acting elements are defined as DNA sequences adjacent to a gene that directly or indirectly regulate the expression of the gene by modulating the binding of a variety of trans-acting elements, so called transcription factors. The promoter is one of the most important cis-acting elements and generally considered as a nucleotide sequence region that is located 5' upstream to the transcription start site of a gene. The promoter contains the binding site for RNA polymerase II and initiates the transcription of the gene. It also contains several well-conserved sequence elements, such as the TATA box around base position −30 and the CAAT box around base position −70 relative to the transcription start site (+1) (Joshi 1987). The TATA box is essential for accurately positioning the initiation of transcription. The CAAT box is not present in all promoters but is in some promoters replaced with a GC-rich element. In addition to these basic elements, the promoter also contains additional sequence elements that are responsive to environmental signals and to physiological conditions, such as drought stress, heat shock, cold stress, availability of nutrients, light, and ion strength. Some promoters also contain sequence elements that confer tissue- or cell-specific gene expression. The promoter is also critical in plant genetic engineering in that a gene of interest can be expressed in an important agronomic plant in ways that the gene expression is modulated in terms of expression level, tissue- or cell-specificities, developmental stage dependence, and responsiveness to a specific environmental stimulus.

Translationally controlled tumor protein (TCTP) is one of the recently identified growth-related proteins in plants and animals. It is a highly conserved cytosolic protein among various organisms, including man, animals, plants, and yeast (Woo et al. 1997) and very stable against heat, pH, ionic strength, and even against protease, suggesting that it has a very compact globular structure. One interesting characteristic of the TCTP protein is that its expression is closely related with growth condition of cells. In accordance with this, the TCTP protein has been originally isolated from rapidly growing tissues, including cancerous tissue in animals and callus tissue, apical stem and leaf, and root meristem tissue in plants. These observations suggest that it may have a regulatory role in cell proliferation (Woo et al. 1997; MacDonald et al. 1995; Hughes et al. 1993). However it has been later found that the TCTP protein is also expressed in healthy animal and plant tissues and that the expression is regulated by calcium ion at both the transcriptional and post-transcriptional levels (Wu et al. 1999; Sanchez et al. 1997; Xu et al. 1999). The TCTP protein associates with cytoskeletal microtubular networks (Gachet et al. 1999; Gachet et al. 1997) via direct interaction with α- and β-tubulins in a $Ca^{2+}$-dependent manner in animal cells. As a whole the TCTP protein is an acidic protein with a pI of about 4.0, but a domain of about 50 amino acids in the central region is highly basic with a pI of 9.4. This basic domain physically interacts with the tubulins (Gachet et al. 1999). Taken together, these observations propose that the TCTP protein has a housekeeping role in the regulation of cell growth and differentiation. Many TCTP genes and gene sequences have been isolated from various tissues in animals and plants (Sage-Ono et al. 1998; Tamaoki et al. 1997; Woo et al. 1997). However, except for a few cases, only the TCTP gene sequences have been deposited in the databases without detailed molecular biological and functional analysis, especially in plants. A pea TCTP gene is expressed to a high level in rapidly dividing cells within the root cap (Woo et al. 1997). In a short-day plant Japanese morning glory (*Pharbitis nil* cv. Violet), the TCTP mRNA accumulates to a high level when the plant is grown in the dark, but the expression level decreases to an undetectable level in the light (Sage-Ono et al. 1998), suggesting that the TCTP has a role in the light-regulated growth at least in this plant species. Except for these two cases, no detailed studies have been reported in plants.

We recently found that a pea TCTP protein directly interacts with a Rab-like small molecular weight GTPase (small GTPase), pea Pra3 that is light-repressible and predominantly expressed in the epicotyls of dark-grown pea seedlings. Northern blot analysis revealed that the pea TCTP gene is transcribed to a high level in all plant parts examined, such as stems, leaves, and roots, but with the highest transcript level in the meristem tissue of root tip. In addition, the transcription was further induced with a factor of 2–3 by a 15% PEG treatment that mimics the drought stressed condition in plants. The same expression patterns were also observed with a tobacco TCTP gene homolog. These results, taken together with the previous reports (Sage-Ono et al. 1998; Woo et al. 1997), suggested that the promoter of the plant TCTP genes would be useful for the expression of foreign genes of interest in transgenic plants with high economic value. In an attempt to investigate the regulatory mechanism on the TCTP gene expression in plants and to evaluate the potential of the TCTP promoter in plant genetic engineering, we isolated a DNA sequence from the 5' untranscribed region of a TCTP gene from Arabidopsis, defined the promoter region by serial deletions, and examined the expression level and pattern of the reporter gene placed under the control of the TCTP promoter in transgenic plants.

The Arabidopsis TCTP promoter region contains a typical TATA consensus sequence at base position −120 relative to the ATG start codon. However, neither CAAT box nor GC-rich element is identified at appropriate positions in the 5' untranscribed region. Consistent with the previous observations, a couple of light-responsive elements are identified. The TCTP promoter led to a high-level expression of a reporter gene in all plant parts with the highest transcription level in the meristem tissue of root tip, which is consistent with the previous result in pea plant (Woo et al. 1997). Several different TCTP promoter constructs with deletions from the 5' end were linked to the reporter gene, and the expression cassettes were examined in transgenic Arabidopsis plants. A minimum of 300 bp was enough for the high-level expression of the reporter gene. In addition, the 300-bp promoter element exhibited the most predominantly localized expression in the root meristem. These characteristics indicate that the TCTP promoter can be utilized to drive a high-level expression of genes of interest in appropriate host plants.

With recent technical developments and advances in plant tissue culture and plant genetic engineering, it is now a routine experiment to introduce a useful gene into a desired host plant with an aim to improve productivity and quality that can't be easily achieved by classical breeding. To achieve this goal, a foreign gene is precisely linked to the TCTP promoter to make the gene expressible under the control of such promoter in transgenic plants.

SUMMARY OF THE INVENTION

The present invention provides a nucleic acid molecule from the 5' untranscribed region of an Arabidopsis TCTP gene that ensures the high-level expression of a foreign gene properly linked to said nucleic acid molecule in transgenic plants. With the present invention, it is possible to express a gene of interest to a high level in whole plant as well as selectively in the meristem tissue of root tip.

Any desired gene is placed under the control of the TCTP promoter in an appropriate expression cassette, and the recombinant expression cassette is introduced into a host plant by various transfection methods, well-known techniques in the art. The promoter in this invention is also responsive to and further induced with a factor of 2–3 by drought stress. Regarding this, the present invention can be particularly utilized to engineer a gene of interest to be expressed to a certain level under normal condition and to be further induced by drought stress.

Root growth is critical for the yield of agronomic plants. The TCTP promoter according to the present invention can be used to accelerate root growth, especially under drought stress or water deficit. In one aspect of the invention, the TCTP promoter can be utilized to express genes involved in the stimulation and regulation of root growth and development.

The present invention also provides the expression cassettes and plasmids comprising the TCTP promoter as described above that are introduced into genetically engineered plants.

Another aspect of the present invention relates to transgenic plant cells and plants containing any gene of interest placed under the control of the TCTP promoter and to experimental processes to isolate the TCTP promoter sequence from Arabidopsis plant.

With the present invention, it is possible to engineer a plant so that it can produce a large amount of a biologically important material, exhibit improved growth rate and development, or show enhanced adaptability to environmental changes.

BRIEF DESCRIPTION OF THE DRAWINGS

FIG. 2 shows the nucleotide sequence of the Arabidopsis TCTP promoter. The DNA molecule was isolated by polymerase chain reaction (PCR) using a pair of specific primers from the Arabidopsis genomic DNA. The nucleotide sequence is given in SEQ ID NO: 1 and deposited in the GenBank database (Accession No. AF237735). The start codon of the TCTP gene is in bold face, and a putative TATA box consensus sequence is double-underlined. The promoter does not have the typical CAAT element but has a couple of putative light-responsive elements as indicated. A putative GA-responsive element is also recognized. PCR primers used to synthesize TCTP promoter constructs with different lengths (see FIG. 3) are indicated by arrows in the 5' to 3' direction. Primer 1; −1990 to −1963, primer 2; −1312 to −1296, primer 3; −681 to −663, primer 4; −303 to −284, primer 5; −1 to −28. Numbers indicates base positions relative to the start codon of the TCTP gene.

DETAILED DESCRIPTION OF THE INVENTION

Molecular biological and biochemical studies, mostly in animals and a few cases in plants, have suggested that translationally controlled tumor proteins (TCTP) may have a housekeeping role in the regulation of growth and development. Although they have been originally isolated from tissues that exhibit abnormally rapid growth, it has been later confirmed that they are also expressed to a high level in normal cells and that their expression is regulated both at the transcriptional and translational levels. In plants, the physiological role of the TCTP protein is not well established yet. In a few cases in which some molecular biological studies have been performed, the TCTP gene expression is regulated by light and predominantly expressed in the rapidly dividing cells, such as those in root meristem tissue, suggesting that the TCTP protein is involved in cell division and differentiation in plants.

The term "promoter" is considered as a nucleotide sequence located in the 5' upstream region of a structural gene that leads to the initiation and regulation of the gene expression. The promoter in general contains several well-conserved sequence components. One is the TATA box that is located about 10–40 bases upstream to the transcription start site (+1) and has a consensus of 5'-TATAAT-3'. The other is the CAAT box with a consensus of 5'-CCAAT-3' in most cases. It is usually positioned about 40–110 bases upstream to the transcription start site. A third sequence component, a GC-rich region, is also present in some promoters. In other promoters, the CAAT box is replaced with a AGGA box with the sequence of 5'-AG(or T)NGA-3', where N is any of the four nucleotides. Although the promoter is not always enough for directing the gene expression, it is the most critical component for the regulation of gene expression. Therefore elucidation of the promoter system is a prerequisite for the understanding of the regulatory mechanism underlying a gene expression in plant growth and development. Furthermore, the promoter systems are important components in plant genetic engineering in that the expression of a given gene is modulated by a specific promoter.

The present invention provides a strong constitutive promoter isolated from an Arabidopsis TCTP gene. The promoter directs the high-level expression of a gene in all plant parts when the gene is properly linked to the promoter. In addition, the promoter activity is further induced by a factor of 2–3 under the drought stress, especially in stems.

"Properly linked to the promoter" indicates that a structural gene of interest is ligated to the 3' end of the promoter sequence so that the expression of the gene is regulated by the promoter. The regulation of the gene may be constitutive or inducible, depending on the promoter linked to the gene. The inducible expression may be controlled by environmental factors, such as cold, drought, or pathogen infection, etc. The expression of a gene may be also regulated in a developmental stage-dependent manner or in a cell- or tissue-specific manner.

The regulatory role or strength of the promoter for the expression of a structural gene can be examined either at the transcriptional or translational level. To examine it at the transcriptional level, DNA-RNA hybridization technique can be employed. To do this, total RNA or mRNA is isolated from appropriate plant materials, run on an agarose gel, transferred onto a supporting membrane, and probed with a radio-labeled DNA probe. In the assays at the translational level, crude extracts or a purified protein is isolated from plant materials and examined using a specific antibody, a well-known technique to the art.

The promoter in the present invention is designated as the TCTP promoter. The TCTP promoter is derived from the 5' upstream region of an Arabidopsis TCTP gene and has a nucleotide sequence given in SEQ ID NO: 1 (GenBank Accession No. AF237735). The nucleotide sequence can be isolated by PCR, a commonly used skill in the art, using the Arabidopsis genomic DNA as template and a pair of specific PCR primers. Partial sequence regions of said nucleotide sequence is also synthesized in the same way.

The present invention also relates with nucleic acid molecules that hybridize under high stringent condition to the nucleic acid molecule with the nucleotide sequence given in SEQ ID NO: 1. The term "hybridize under high stringent condition" indicates that such nucleic acid molecules hybridize to the nucleic acid molecule through base pairing under conventional hybridization conditions, as described in Sambrook et al., (Molecular Cloning: A Laboratory Manual, $2^{nd}$ Ed., Cold Spring Harbor Laboratory, Cold Spring Harbor, N.Y., 1989). Nucleic acid molecules hybridizing with the above nucleic acid molecule include in general those from any plants, preferentially from plants of interest in agriculture, forestry, and horticulture.

To isolate a nucleic acid molecule that hybridize to the nucleic acid molecule given in SEQ ID NO: 1, a genomic DNA library is screened using the above-described nucleic acid molecule as probe through the colony hybridization method, a molecular biological technique well known to the art.

The nucleic acid molecule in the invention also relates with those that are degenerate to the nucleic acid molecule given in SEQ ID NO: 1. The term "degenerate" means that the nucleotide sequences of such nucleic acid molecules differ from the above-described nucleic acid molecule in one or more base positions and highly homologous to said nucleic acid molecule.

"Homologous to said nucleic acid molecule" suggests that the nucleotide sequence of a nucleic acid molecule is closely related with said nucleic acid molecule with at least 70%, particularly 80% or higher, identity in the nucleotide sequences.

The present invention also includes any derivatives of the above-described nucleic acid molecule that are generated by insertions, deletions, base substitutions, or recombinations.

Furthermore, the invention also related with recombinant DNA molecules, comprising the TCTP promoter functionally linked to a reporter gene, which is useful to evaluate said promoter in transgenic plant cells or plants.

In one embodiment of the invention, the TCTP promoter is operably linked to a desired gene such that the gene is expressed to a high level in all plant parts, especially in the root meristem tissue, to improve plant growth.

The present invention also relates to the expression cassettes and plasmids comprising the TCTP promoter that can be used for the transformation of plant cells.

With recent rapid advances in plant tissue culture and genetic engineering, it is possible to introduce a gene of interest into virtually any of economically important plants. For this purpose, regulatory elements for the expression of a gene, such as the TCTP promoter in the present invention, are critical.

Therefore, the present invention provides:
1. A nucleic acid molecule from the 5' upstream region of an Arabidopsis TCTP gene, comprising a nucleotide sequence given in SEQ ID NO: 1, and
2. An *E. coli* strain XL1-Blue transformed with the vector pTCTP-2K and deposited as KCTC 0807BP. The vector pTCTP-2K contains a nucleic acid molecule with the nucleotide sequence given in SEQ ID NO: 1.

EXPERIMENTAL PROCEDURES

Construction of the Expression Cassettes

Figure 3:
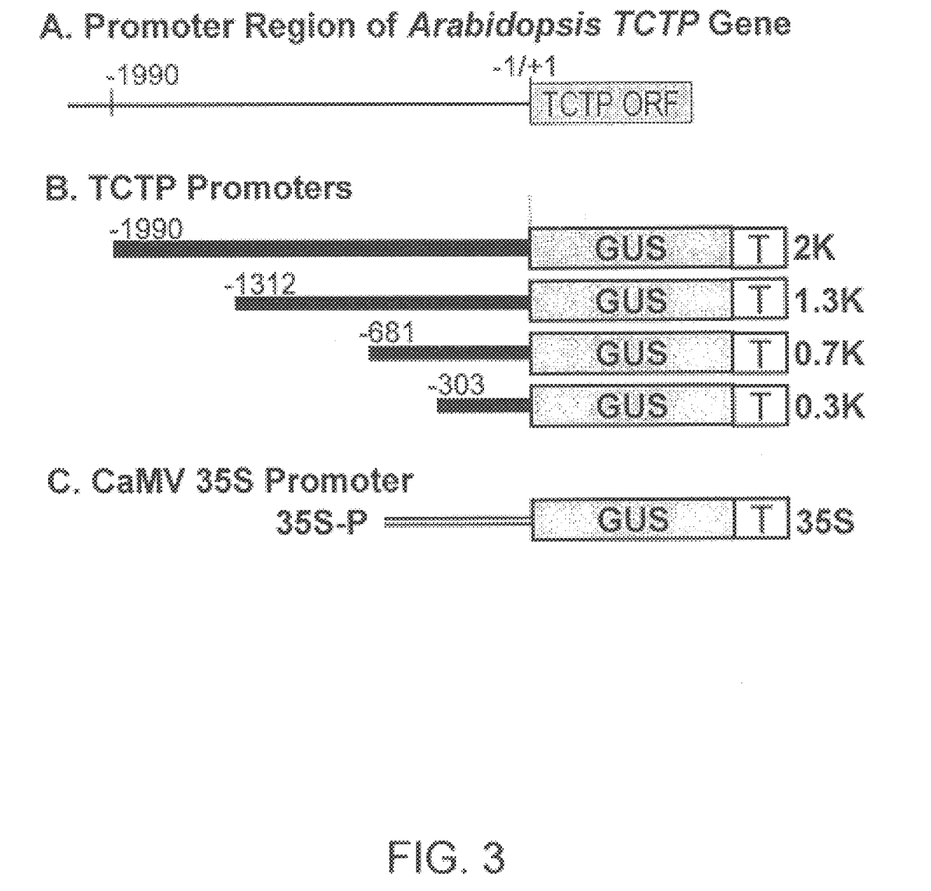
FIG. 3 shows the schematic diagram of the TCTP promoter constructs generated and tested in the present invention. Promoter regions with lengths of 2 kbp, 1.3 kbp, 0.7 kbp, and 0.3 kbp were isolated by PCR runs and transcriptionally linked to the GUS gene sequence in the pBI-based promoterless vector. All the resultant expression cassettes were verified by direct DNA sequencing. The 35S promoter was used as a control. Numbers indicate base positions starting from the (1+)ATG codon as in FIG. 2. T; nos terminator. A; an Arabidopsis TCTP gene and its 5' untranscribed region, B; TCTP promoters generated in this work, C; CaMV 35S promoter used as a control.

Plant TCTP genes are constitutively expressed in all plant parts to an extremely high level. Their expression is also regulated by drought stress and light. These characteristics suggest that the TCTP promoter could be very useful for expression of desired genes in genetically engineered plants. A DNA fragment of about 2.2 kbp was isolated from the 5' upstream region of an Arabidopsis TCTP gene by PCR run using Arabidopsis genomic DNA and a pair of specific primers. The full nucleotide sequence was confirmed by DNA sequencing and deposited in the GenBank database (Accession Number: AF237735). Several promoter sequences with different lengths were also constructed by a series of PCR runs (FIGS. 2 and 3). The TCTP promoter sequences were then transcriptionally fused to a gene sequence encoding the β-glucuronidase (GUS) in a pBI-based promoterless vector. The expression cassettes containing the GUS-TCTP promoter fusions were verified by DNA sequencing.

Plant Materials and Growth Conditions

The *Arabidopsis thaliana* ecotype Columbia (Col-0) was used for transformation. Sterilized seeds were germinated and grown on 0.5× Murashige and Skoog medium containing 1% agar and Suc. All Arabidopsis cultures were maintained in a controlled environment culture room at 22° C. with the humidity of 70% and the photoperiod of 12 hours.

Plant Transformation

The GUS-TCTP promoter fusion expression constructs were introduced into Arabidopsis plants grown under sterile condition. The Agrobacterium-mediated transformation was performed by a simplified floral dip method (Clough and Bent, 1998). The expression constructs were first transformed into *Agrobacterium tumefaciens* strain LBA4404, and the cells containing the expression constructs were used to infect Arabidopsis plants. Kanamycin and cefotaxime were used for selection of transformants at 200 mg/ml and 500 mg/ml, respectively.

RNA Extraction and Northern Hybridization

Total RNA samples were isolated from appropriate plant materials using the RNasey Plant Total RNA Isolation Kit (Qiagen, Valencia, Calif.) according to the procedure provided by the manufacturer. RNA samples were denatured in MOPS buffer (20 mM MOPS, 8 mM sodium acetate, 1 mM EDTA) supplemented with 50% (v/v) formamide and 2.2M formaldehyde at 65° C. for 10 min and fractionated on a 1% agarose gel prepared in the same denaturation buffer. The probes were prepared by random priming in the presence of α-[$P^{32}$]dATP. Transfer onto Hybond-N membrane and subsequent procedures were carried out as previously described (Sambrook et al. 1989).

DNA Extraction and Southern Hybridization

Genomic DNA was isolated from Arabidopsis plants using the DNeasy Plant Mini Kit (Qiagen) as described by the manufacturer but with some modifications. Briefly, plant materials were ground under liquid nitrogen to a fine powder using mortar and pestle. The powder was then transferred to an Eppendorf tube, and the liquid nitrogen was allowed to evaporate. Five hundred µl of buffer AP1 and RNase A solution, supplied by the manufacturer, was added and vigorously vortexed. The mixture was then incubated at 65° C. for 10 min with frequent inversions. After cell lysis, 160 µl of buffer AP2 was added, and the final mixture was incubated on ice for 5 min. The above step is to precipitate detergent, proteins, and polysaccharides. The precipitates were removed by centrifugation for 5 min at maximal speed. The supernatant was then applied to the QIAshredder spin column and centrifuged for 2 min at maximal speed. The flow-through was mixed with 0.5 vol of buffer AP3 and 1 vol of absolute ethanol, applied onto the DNeasy mini spin column, and centrifuged for 1 min at 8,000 rpm. Five hundred µl of buffer AW was added to the column and recentrifuged for 2 min at maximal speed to dry the column membrane. To elute the genomic DNA, 100 µl of preheated (65° C.) buffer AE was directly applied to the membrane and incubated at room temperature for 5 min. The column was then centrifuged for 1 min at maximal speed. The resultant genomic DNA solution was extracted with an equal volume of phenol:chloroform:isoamyl alcohol (25:24:1) and precipitated with ethanol at room temperature for 5 min, and the DNA was recovered by centrifugation.

The genomic DNA was digested with EcoRI and HindIII whose recognition sites were not present in the GUS gene in the expression cassettes used to transform Arabidopsis plants. Five units of each restriction enzyme was used per 1 µg of genomic DNA, and the mixture was incubated at 37° C. for 4 hours. To get better resolution on the agarose gel, the digestion mixture was precipitated with ethanol, and the pellet was rinsed with 70% ethanol 2 times and air-dried. The sample was dissolved in 1× loading buffer and loaded onto a 0.8% gel. The probe used was a radio-labeled GUS gene sequence. The GUS gene sequence was used as probe instead of the TCTP promoter sequence since the Arabidopsis transgenic plants contained intrinsic TCTP promoter sequences.

Histochemical Assays of GUS Activity

Whole plants or specific plant parts were soaked in the X-gluc solution (0.1 M sodium phosphate, pH 7.0, 10 mM EDTA, 0.5 mM potassium ferricyanide, 0.5 mM potassium ferrocyanide, 0.1% Triton X-100, 0.3% 5-bromo-4-chloro-3-indolyl glucuronide, and 20% methanol) for 2–4 hours. The Triton X-100 was freshly added just before use. The plant materials were then soaked in absolute ethanol at room temperature overnight to remove chlorophyll. Ethanol was changed 4–5 times during the incubation. The destained sample was examined under light microscope and photographed if required.

Fluorometric Analysis of the GUS Activity

Expression level of the GUS activity was accessed by the fluorescent method basically as described by Jefferson (1988). The 4-methylumbelliferyl-β-D-glucuronide(MUG) was used as fluorogenic substrate for the GUS activity. Plant crude extracts were prepared as follows. Plant materials were ground under liquid nitrogen to a fine powder and extracted with cell lysis buffer (0.5 M Tris.Cl, pH 7.5, 1 mM DTT, 1 mM 1,2-diaminocyclohexane-N,N,N',N'-tetraacetic acid, 10% glycerol, 1% Triton X-100, 1 mM EDTA). Cell lysis buffer of 200 µl was used for 1 gram of fresh plant material. Any insoluble material and cell debris were removed by centrifugation for 15 min with maximal speed at 4° C. The supernatant was used for fluorometric measurement without further purification. Protein concentration was determined using the Bradford method. The fluorometric measurement was performed as previously described (Jefferson, 1988).

RESULT

Dual Expression Patterns of the Plant TCTP Gene: Constitutive and Inducible

The translationally controlled tumor proteins (TCTPs) have unique structural and functional characteristics, although the exact physiological function was not precisely defined yet. Since they have a high amino acid sequence homology (60–70% throughout the whole sequences) among various organisms, their physiological roles in plants and animals are expected to be identical. The TCTP proteins are very stable, even against proteases. They are highly acidic cytosolic proteins with a pI value of 4.0 but have a domain in the central region that is highly basic with a pI value of 9.2. This basic domain directly interacts with tubulins, and this interaction has been suggested to be involved in cell division and differentiation. The TCTP proteins are highly expressed in rapidly growing tissues, such as cancerous cells in animals and callus tissue in plants. They are also highly expressed even in normal tissues but with some tissue-dependent variations. In plants, the TCTP expression is regulated by light, probably in a species-specific manner. In addition we recently observed that the TCTP expression is also induced by a 15% PEG treatment, suggesting a role for the TCTP proteins in stress responses in plants. Of particular interest is that the TCTP gene is transcribed to an extremely high level at least in tobacco, pea, and Arabidopsis plants which we examined, and probably in all higher plants.

With an aim to examine the regulatory mechanism for the TCTP gene expression and to develop a useful promoter system for plant genetic engineering, the 5' untranscribed region of a TCTP gene was isolated from Arabidopsis, and its regulatory role on the report gene expression was investigated in terms of tissue specificities, responsiveness to environmental factors, and relative activity.

Figure 1:
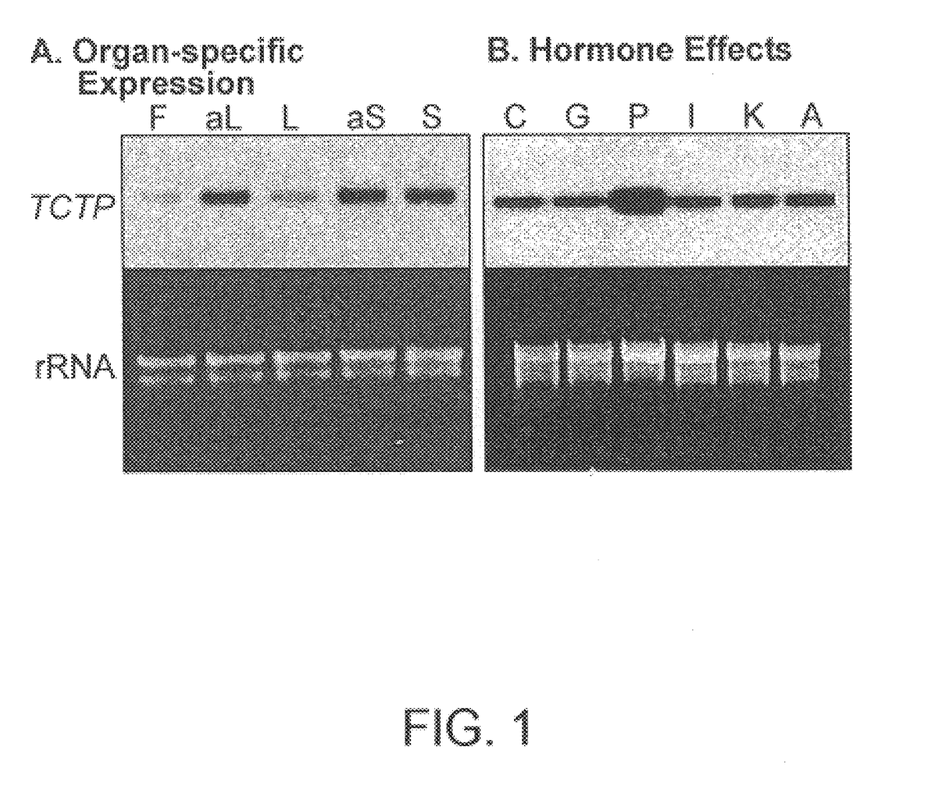
FIG. 1 shows Northern blot analyses of a pea TCTP gene expression. (A) Light-grown pea plants were dissected into leaves, apical leaves, stems, apical stems, and floral organs. Total RNA was isolated separately from each plant part. Three μg of total RNA was loaded onto each lane and probed with $P^{32}$-labeled TCTP gene sequence. The HiBond-$N^+$ filter was exposed for 30 min in this Northern blot analysis. (B) Pea plants were grown in the presence of various plant growth hormones at physiological concentrations. Stem parts from each treatment were assayed. C; untreated, G; GA3, P; 15% PEG, I; IAA, K; kinetin, A; ABA. Similar results were obtained with other plant parts (roots and leaves).

We first examined the transcription level and pattern of the TCTP gene in the pea plant by Northern blot analysis. The transcription level was extremely high in all plant parts tested but with some variations in different plant parts, relatively higher level in stem and lower level in floral organ (FIG. 1A). The TCTP gene was most highly transcribed in rapidly growing parts, such as apical stems and leaves. This suggests that the TCTP protein is related with plant growth and development, which is also consistent with the previous reports (Woo et al. 1997). When the plants were treated with various plant hormones, none of them affected the transcription level except for a 15% PEG treatment that mimics drought condition in plants. The 15% PEG treatment induced the transcription by a factor of 2–3 times (FIG. 1B). Of particular interest is the fact that the transcription level is very high as a whole. In the Northern blot analysis as shown in FIG. 1, only 3 µg of total RNA was loaded onto each lane, whereas 15–20 µg of total RNA is usually used in ordinary Northern blot analysis. In addition, exposure for 10–20 min was enough for the detection of the TCTP transcript. All together, these observations indicate that the TCTP gene is constitutively expressed to a high level in all plant tissues, and its expression is further induced by environmental factor (s), such as drought stress.

Surprisingly light did not show any significant effect on the TCTP transcription in the pea plant, which is inconsistent with the previous result observed with the Japanese morning glory plant (Sage-Ono et al. 1998). The same result was also obtained with a tobacco TCTP gene. It is therefore possible that the light effect is dependent on plant species. Alternatively, plants may have several TCTP genes each of which is regulated by different mechanisms. Our Southern blot analyses of pea, tobacco, and Arabidopsis revealed that each plant species has either a single copy gene (pea, Arabidopsis) or at most two copies (tobacco, Japanese morning glory) (data not shown), preferably supporting the first possibility.

Taken all together, it is evident that plant TCTP genes are constitutively transcribed to an extraordinarily high level in all plant parts, and the transcription seems to be further up-regulated by environmental factors, suggesting an essential regulatory role for the TCTP protein in cell proliferation and differentiation. It was also proposed that the promoter of plant TCTP genes was so strong that it could be utilized to express a protein of interest in a large quantity in genetically engineered agronomic plants and to improve plant growth and development.

The Promoter Region of an Arabidopsis TCTP Gene

An efficient way to test the regulatory role of a promoter is to construct a chimeric fusion, in which a structural gene is functionally linked to the promoter, and introduce this expression construct into transgenic plants. The activity or expression level of the structural gene product in transgenic plants can be easily analyzed in vitro. Reporter genes that are frequently employed in this approach usually encode enzymes that catalyze the production of easily detectable materials. The product is then used to deduce the activity of the fusion construct and therefore to measure the regulatory activity of the promoter. One of the most widely used reporter systems for the promoter analysis is the GUS gene fusion system (Jefferson, 1988). In this reporter system, a promoter or a putative promoter element is fused to the gene sequence encoding an E. coli β-glucuronidase (GUS). The GUS hydroxylates a variety of β-glucuronides and has many useful biochemical properties to be used as a reporter. It is absent from virtually all higher plants, if not all, and very stable against detergents, pH, and ionic conditions. In addition, it does not require any supplementary cofactors. It is absolutely localized in the cytoplasm and does not require any post-translational modifications. These properties make the GUS system an universal reporter that can be used in any higher plants and analyzed even in crude extracts roughly isolated from plant materials.

We decides to isolate the promoter region from the 5' upstream region of the TCTP gene in plants to examine its regulatory role in gene expression and to develop an useful promoter system to be used in genetic engineering in plants. We originally isolated a pea TCTP gene based on the ability of the TCTP protein to directly interact with a stress-related Ras-like small GTPase, pea Pra3 (Nagano et al. 1995; Yoshida et al. 1993). Molecular biological analysis revealed that it is constitutively expressed to a high level in all plant parts. Database search identified a TCTP gene homolog on chromosome 3 in Arabidopsis. Based on the nucleotide sequence of the genomic clone MGL6 (Accession Number: AB022217), a pair of specific primers were designed, and the promoter region of 2181 bases was amplified by PCR using Arabidopsis genomic DNA as template. The primers used were 5'-GCCGGATCCTGACCCAACCCAAGTGTCCC (the 5' end primer, SEQ ID NO. 2) and 5'-GCCGGATCCAAGATCTTGGTACACCAACATG (the 3' end primer, SEQ ID NO. 3) with BamHI recognition sites at each 5' end for cloning purpose. The PCR product was cloned into pGEM7Z(+), resulting in the pTCTP-2K vector, and its nucleotide sequence was confirmed by DNA sequencing and deposited in the GenBank database (GenBank Accession No. AF237735). The 3' end of the DNA fragment contains a short coding sequence encoding the first 7 amino acids of the putative Arabidopsis TCTP protein.

The putative TCTP promoter region contains a typical TATA box at base position −120 relative to the ATG codon (FIG. 2). One putative CAAT box is located about 270 bases upstream to the TATA box. However it does not seem to be functional in the regulation of the TCTP gene expression since its location is not well fit to that of the experimentally proven CAAT boxes in plant genes. In addition, the nucleotide sequence around the putative CAAT box, 5'-GAACAATCA, is somewhat diverse from the typical one in plant genes, 5'-GG(T/C)CAATCT. A couple of light-responsive elements are recognized in the TCTP promoter that have been experimentally confirmed in other plant genes, such as 5'-AGAAACAA and 5'-AGCTATCCA at base positions −1352 and −767, respectively (Conley et al. 1994; Park et al. 1996). It is not clear whether the light-responsive elements are functional or not, but they may be related with the previous observations with the Japanese morning glory plant, in which the TCTP gene transcription is drastically repressed by light. In addition, there is a GA-responsive element at base position −1396, 5'-CCTTTTG, as has been confirmed in glutelin genes in rice (Takaiwa et al. 1991).

Plant Organ-Dependent Expression

To examine the regulatory role of the TCTP promoter in gene expression, a region of about 2 kbp was reamplified from the pTCTP-2K vector using the 3' end primer, primer 5, and the 5' end primer, primer 1 (FIG. 2). The resulting PCR product was cloned into a pBI-based promoterless vector in a way that the 3' end of the promoter is transcriptionally fused to the sequence encoding the GUS. The resultant expression cassette (2K in FIG. 3) was then transformed into Arabidopsis plants, and a homozygotic line was isolated through sequential selections by kanamycin. In addition to the 2K construct, a few more constructs were designed by deleting nucleotide sequences from the 5' end of the 2K construct to determine the boundaries of the TCTP promoter and to define any consensus sequences required for interaction with trans-acing factors. Each construct was generated by PCR run using a pair of appropriate primers as indicated in FIG. 2. The primer 5 was used as the 3' end primer for all the promoter constructs. The 5' end primers used for the 1.3K, 0.7K, and 0.3K constructs were primers 2–4, respectively (FIG. 2). The resultant expression cassettes are shown in FIG. 3. The 35S promoter was included as a positive control (FIG. 3C), and the promoterless vector without any inserts was used as a negative control.

Figure 4:
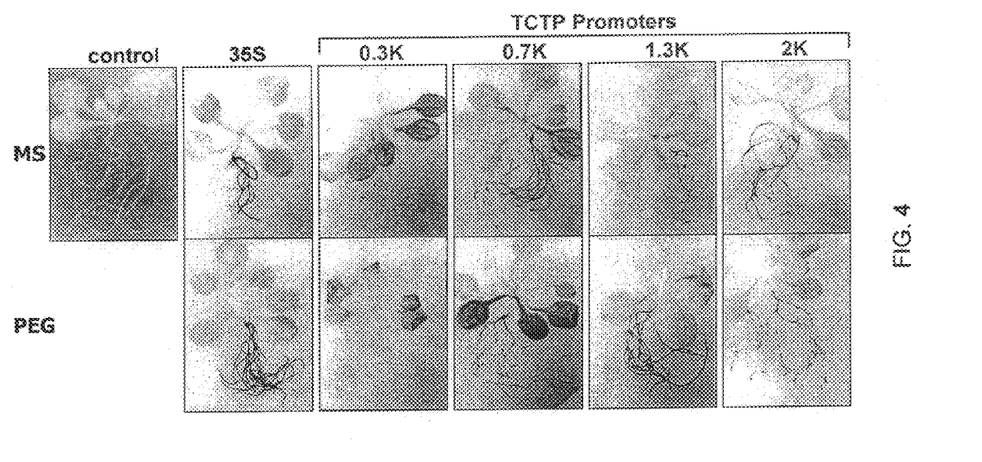
FIG. 4 shows the GUS activity in whole plants detected by histochemical assay. The expression cassettes containing the GUS-TCTP promoter fusions were transformed into Arabidopsis plants, and homozygotic lines were isolated through repeated kanamycin selections. Whole plants were used for the GUS staining for 4 hours and destained in absolute ethanol at room temperature overnight. The lower panel shows the transgenic plants treated with 15% PEG. The control plant was transformed with the promoterless vector without the TCTP promoter sequence.

The GUS activities of the transgenic plants were then assayed according to the standard method using whole plants (Jefferson and Wilson 1991). It was evident that the TCTP promoter is functional in all plant parts, including leaves, stems, cotyledons, and roots, with the most dense staining in vascular tissue like with the 35S promoter. The staining pattern was indistinguishable from that of the 35S promoter (FIG. 4). One difference is that the root meristem tissue is the most densely stained in the transgenic plants containing the TCTP expression cassettes, but those containing the 35S promoter did not exhibit such a distribution pattern. In addition, blue spots became clearly visible within a few minutes after soaking in the staining solution in case of the transgenic plants containing the TCTP promoter, much faster than those in the 35S control transgenic plants. These indicate that the TCTP promoter is at least as strong as, probably stronger than, the 35S promoter.

A 300-bp Region as a Promoter

Figure 5:
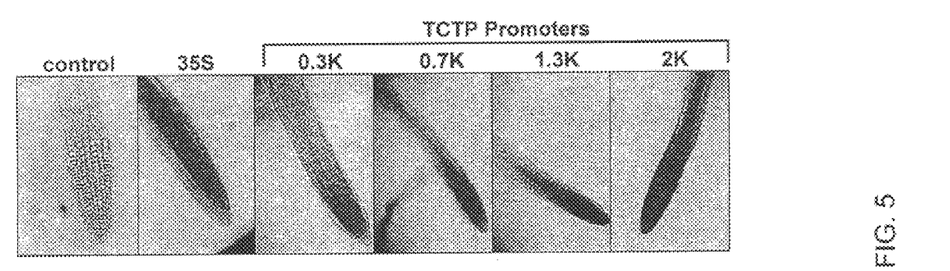
FIG. 5 shows the expression of the GUS gene in roots. Roots were detached from the transgenic plants as used in FIG. 4 and treated in the same way as in FIG. 4. The control plant is also as in FIG. 4.

The GUS activity assays revealed that a TCTP promoter region, as small as 300 bp, is still functional in the regulation of the reporter gene expression and that the activity is not far different from that of the 2K promoter (FIG. 4). Interestingly, the localized expression of the GUS in the root meristem became more prominent as the 5' end sequence is deleted from the TCTP promoter (FIGS. 4 and 5). In roots, the 0.3K promoter induced the GUS expression almost exclusively in the meristem tissue, while the distribution of the GUS activity in other plant organs, such as leaves and stems, was about the same among different promoter constructs (FIG. 4). These observations indicate that the sequence region between base positions −300 and −1 contains cis-acting elements that lead to the localized expression of the TCTP gene in root meristem tissue or that suppress the TCTP gene expression in other tissues.

The 0.3K promoter does not contain any recognizable cis-acting elements except for the TATA box but still exhibit strong regulatory activity in the reporter gene expression. Of particular interest is the predominant expression of the reporter gene in the root meristem. This characteristic is very useful when a desired gene, especially genes involved in root growth and development, is to be selectively expressed in the root meristem tissue.

Relative Strength of the TCTP Promoter

The regulatory function of a promoter during the expression of a structural gene placed under its control can be analyzed more precisely by comparing the GUS activity of the transgenic plant containing the promoter fusion with that of a transgenic plant containing a control promoter fusion. For more accurate measurements, the experimental and control transgenic plants should have equal numbers of insertions of the promoter fusions.

Figure 6:
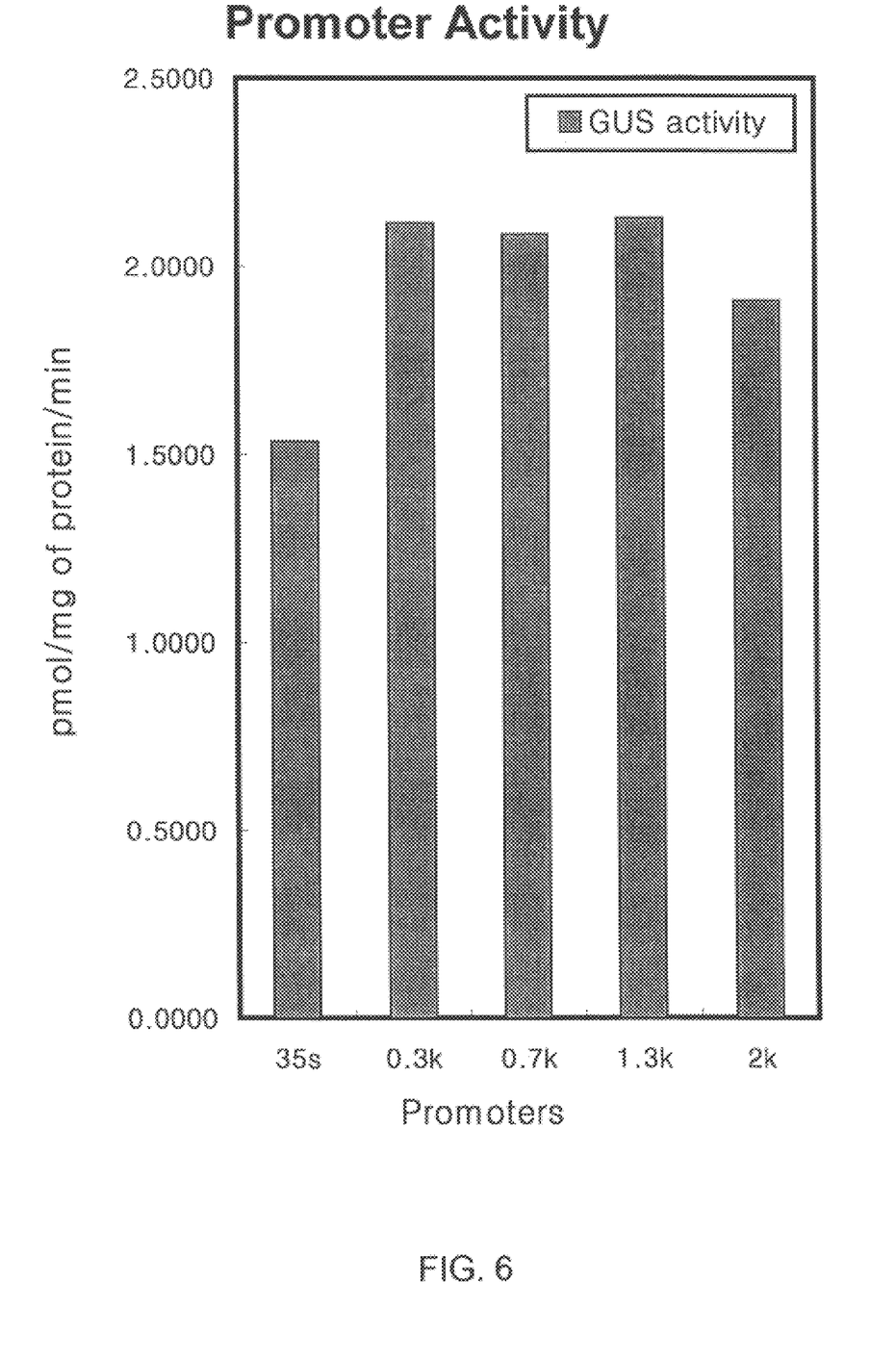
FIG. 6 shows the strengths of the TCTP promoters shown in FIG. 3. The 35S promoter was used as a control. Homozygotic lines of transgenic Arabidopsis plants with single-copy insertions were isolated by Southern blot analysis, including the control plant with the 35S promoter. Crude extracts isolated from light-grown seedlings of transgenic plants were subject to fluorometric GUS assays. GUS activities were calculated as described in Experimental Procedures. Values of three independent measurements were averaged.

We isolate 10–15 homozygotic lines from the transgenic Arabidopsis plants harboring each of the TCTP promoter fusions as well as from that with the 35S promoter fusion. We then measured the insertion numbers in each transgenic plant by Southern blot analysis using genomic DNAs. The copy number of the GUS sequence, rather than that of the TCTP promoter sequence, was accessed since the parental Arabidopsis plant has the intrinsic TCTP promoter sequence used in the present invention. Genomic DNAs were restriction digested with EcoRI and HindIII whose recognition sequences do not exist in the GUS sequence, and restricted DNAs were run on an agarose gel, transferred onto membranes. The Membranes were then proved with a radiolabeled GUS sequence, and transgenic plants that harbor a single insertion event were chosen. The transgenic plants were grown for 9 days in the light, and whole seedlings were used for the fluorometric GUS activity assays. Crude extracts were prepared, and the GUS activities were measured according the standard method as described (Kim and Guiltinan 1999; Jefferson 1988). One such result is shown in FIG. 6.

All the TCTP promoters examined exhibited about 25–38% higher GUS activities than the 35S promoter. Even the 0.3K TCTP promoter was stronger than the control promoter. The 2K TCTP promoter had the lowest activity among the TCTP promoters (FIG. 6), suggesting that a sequence region that includes bases −1300 to −2000 relative to the start codon (+1) contains a negative regulatory element for the Arabidopsis TCTP transcription. These results indicate that the TCTP promoter is superior to the 35S promoter for expression of useful genes in transgenic plants. In addition, the TCTP promoter has an additional advantage. It can lead to predominant expression of useful genes in rapidly growing root tip.

What is claimed is:

1. An isolated nucleic acid comprising a promoter comprising base positions from about 300 bases from about residue 1860 to about residue 2160 of SEQ ID NO: 1, from the 5' untranscribed region of the Arabidopsis TCTP gene which provides high level expression of a foreign gene properly linked to said promoter.

2. An isolated nucleic acid according to claim 1 further comprising the bases from about residues 169 to about 1859 of SEQ ID NO: 1.

3. An isolated nucleic acid according to claim 1 further comprising bases 1481 to 1859 in SEQ ID NO: 1.

4. An isolated nucleic acid according to claim 1 further comprising bases 908 to 1859 in SEQ ID NO: 1.

5. An isolated nucleic acid according to claim 1 further comprising bases 169 to 1859 in SEQ ID NO: 1.

6. A process for the preparation of transgenic plants that express genes under the control of regulatory sequence comprising the about 300 bases on the 5' side of residue 2161 in SEQ ID NO: 1 further comprising:

(i) operably linking a nucleic acid to be expressed to said regulatory sequence;

(ii) incorporating the said operably linked nucleic acid into a cloning vector;

(iii) introducing said vector into a plant cell;

(iv) growing said transformed plant cell.

7. A process according to claim 6 wherein said regulatory sequence is from base 2159 of SEQ ID NO: 1 to between base 169 and base 1859 of SEQ ID NO: 1.

* * * * *